(12) United States Patent
Matossian

(10) Patent No.: US 10,667,954 B2
(45) Date of Patent: Jun. 2, 2020

(54) EAR AND EAR HEADPHONE SHIELDING ASSEMBLY

(71) Applicant: Armand Matossian, Irvine, CA (US)

(72) Inventor: Armand Matossian, Irvine, CA (US)

( * ) Notice: Subject to any disclaimer, the term of this patent is extended or adjusted under 35 U.S.C. 154(b) by 328 days.

(21) Appl. No.: 15/696,564

(22) Filed: Sep. 6, 2017

(65) Prior Publication Data

US 2019/0070039 A1    Mar. 7, 2019

(51) Int. Cl.
*A61F 11/06* (2006.01)
*A61F 11/14* (2006.01)
*H04R 1/10* (2006.01)

(52) U.S. Cl.
CPC .............. *A61F 11/06* (2013.01); *A61F 11/14* (2013.01); *H04R 1/1016* (2013.01); *H04R 1/1083* (2013.01)

(58) Field of Classification Search
CPC ........ A61F 11/06; A61F 11/08; A61F 11/085; A61F 11/12; A61F 11/14; H04R 1/1008
USPC ......... 181/126, 129, 130, 135; 381/370–374, 381/376–380
See application file for complete search history.

(56) References Cited

U.S. PATENT DOCUMENTS

| | | | |
|---|---|---|---|
| 2,727,245 A * | 12/1955 | Suggs | A61F 11/06 2/174 |
| 5,689,831 A * | 11/1997 | Harris | A45D 44/12 2/209 |
| D399,607 S | 10/1998 | Davis | |
| 6,831,984 B2 | 12/2004 | Sapiejewski | |
| 7,571,503 B2 | 8/2009 | Gabriel | |
| 7,869,615 B2 * | 1/2011 | Chang | H04R 1/10 381/371 |
| 8,006,320 B1 * | 8/2011 | Rohbani | A61F 11/14 128/866 |
| 8,306,237 B2 | 11/2012 | Connor | |
| D684,558 S | 6/2013 | Hansson et al. | |
| 8,559,649 B2 | 10/2013 | Kurzweil et al. | |
| 9,020,164 B2 * | 4/2015 | Silberman | H04R 1/1091 381/26 |
| 9,269,342 B2 | 2/2016 | Annumziato et al. | |
| 10,165,345 B2 * | 12/2018 | Slater | H04R 5/033 |
| 2002/0106099 A1 * | 8/2002 | Ma | H04R 1/10 381/371 |
| 2008/0216244 A1 | 9/2008 | Minton | |
| 2008/0263749 A1 * | 10/2008 | Leong | A61F 11/14 2/209 |
| 2010/0189277 A1 * | 7/2010 | Birgersson | A61F 11/12 381/73.1 |
| 2013/0156247 A1 * | 6/2013 | Boyajian | H04R 1/105 381/370 |
| 2018/0140464 A1 * | 5/2018 | Berto | A61F 11/12 |

(Continued)

*Primary Examiner* — Jeremy A Luks

(57) ABSTRACT

An ear and ear headphone shielding assembly, for comfortably laying on an ear with headphones therein, includes a panel and a cushion member. The panel has an inner surface and an outer surface. The inner surface is concavely shaped, while the outer surface is convexly shaped. The panel has a perimeter edge including a top edge, a bottom edge, a first side edge, and a second side edge. The inner surface is shaped as to form a hold to receive an ear such that the ear is adjacent to the inner surface. A cushion member is attached to the perimeter edge as to be coextensive with the top edge, the first side edge and the second side edge, leaving the bottom edge free of the cushion member.

10 Claims, 3 Drawing Sheets

(56) References Cited

U.S. PATENT DOCUMENTS

2018/0325198 A1* 11/2018 Mydell ............... A61F 11/14
2019/0075383 A1*  3/2019 Slater ................ H04R 5/033

* cited by examiner

EAR AND EAR HEADPHONE SHIELDING ASSEMBLY

CROSS-REFERENCE TO RELATED APPLICATIONS

Not Applicable

STATEMENT REGARDING FEDERALLY SPONSORED RESEARCH OR DEVELOPMENT

Not Applicable

THE NAMES OF THE PARTIES TO A JOINT RESEARCH AGREEMENT

Not Applicable

INCORPORATION-BY-REFERENCE OF MATERIAL SUBMITTED ON A COMPACT DISC OR AS A TEXT FILE VIA THE OFFICE ELECTRONIC FILING SYSTEM

Not Applicable

STATEMENT REGARDING PRIOR DISCLOSURES BY THE INVENTOR OR JOINT INVENTOR

Not Applicable

BACKGROUND OF THE INVENTION

(1) Field of the Invention

(2) Description of Related Art Including Information Disclosed Under 37 CFR 1.97 and 1.98

The disclosure and prior art relates to ear and headphone covers and more particularly pertains to a new ear and headphone cover for comfortably laying on an ear with headphones on.

BRIEF SUMMARY OF THE INVENTION

An embodiment of the disclosure meets the needs presented above by generally comprising an ear and ear headphone shielding assembly configured to receive an ear when the ear has a headphone positioned therein. The assembly includes a panel with an inner surface and an outer surface. The inner surface is concavely shaped, while the outer surface is convexly shaped. The panel has a perimeter edge including a top edge, a bottom edge, a first side edge, and a second side edge. The inner surface is configured to receive an ear such that the ear is adjacent to the inner surface. A cushion member is attached to the perimeter edge as to be coextensive with the top edge, the first side edge and the second side edge, leaving the bottom edge free of the cushion member.

There has thus been outlined, rather broadly, the more important features of the disclosure in order that the detailed description thereof that follows may be better understood, and in order that the present contribution to the art may be better appreciated. There are additional features of the disclosure that will be described hereinafter and which will form the subject matter of the claims appended hereto.

The objects of the disclosure, along with the various features of novelty which characterize the disclosure, are pointed out with particularity in the claims annexed to and forming a part of this disclosure.

BRIEF DESCRIPTION OF SEVERAL VIEWS OF THE DRAWING(S)

The disclosure will be better understood and objects other than those set forth above will become apparent when consideration is given to the following detailed description thereof. Such description makes reference to the annexed drawings wherein.

DETAILED DESCRIPTION OF THE INVENTION

Figure 1:
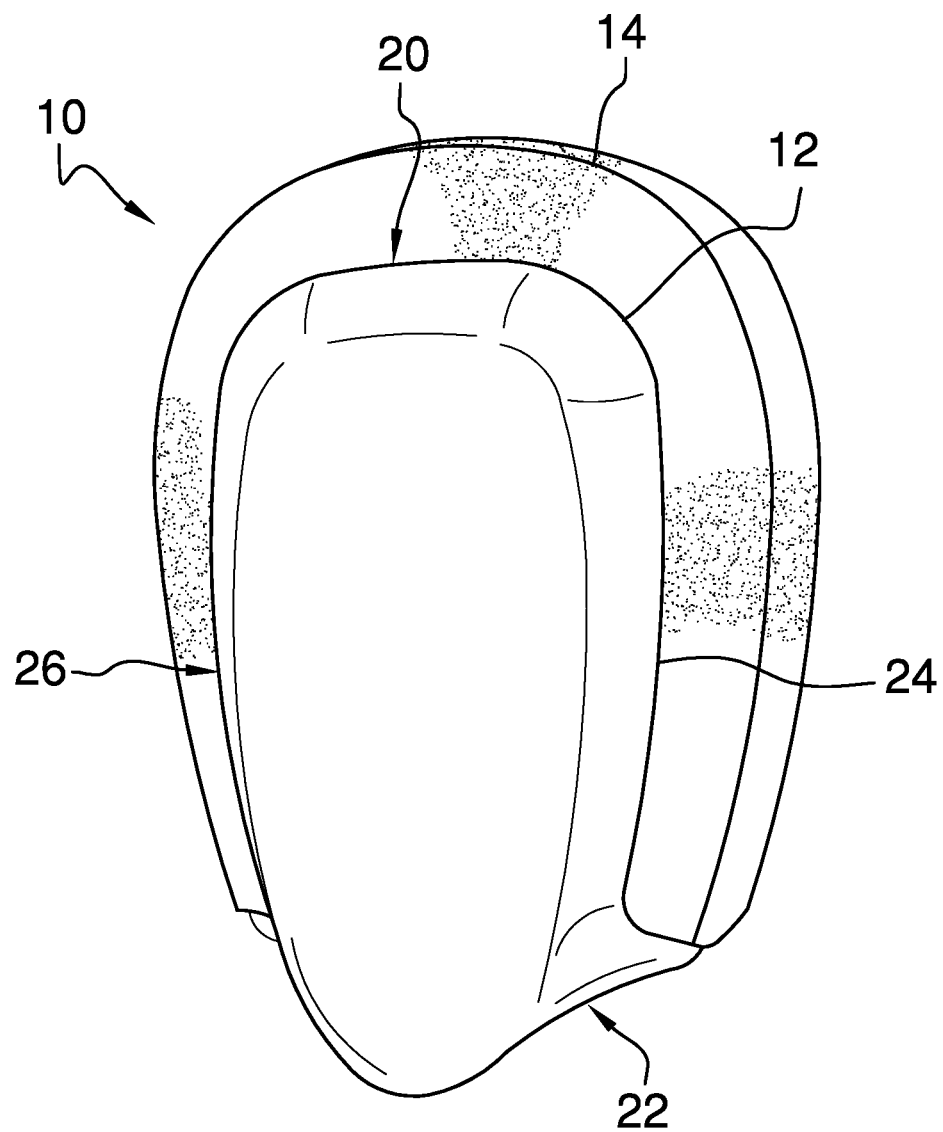
FIG. 1 is a front side view of an ear and ear headphone shielding assembly according to an embodiment of the disclosure.
Figure 2:
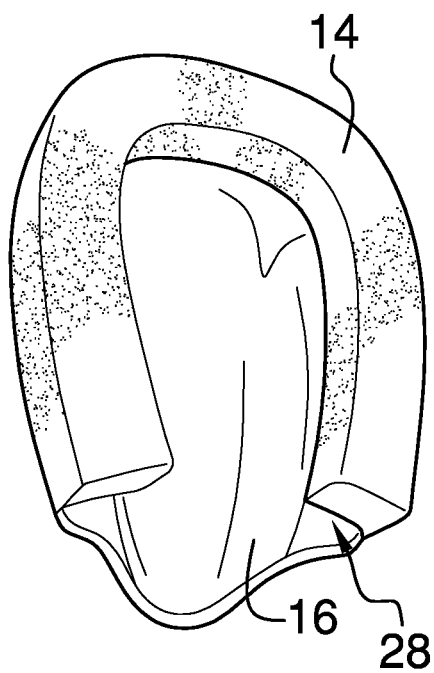
FIG. 2 is a back side view of an embodiment of the disclosure.
Figure 3:
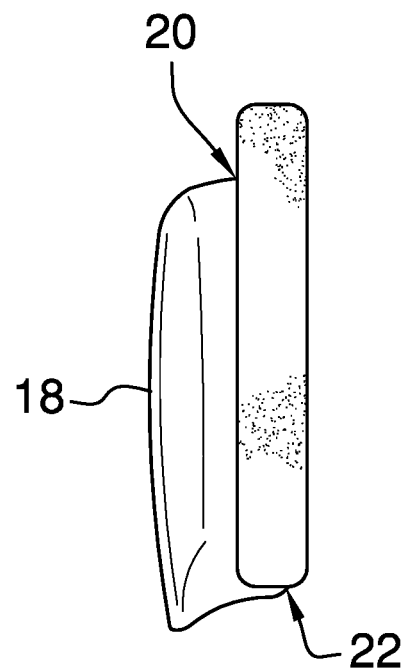
FIG. 3 is a side view of an embodiment of the disclosure.
Figure 4:
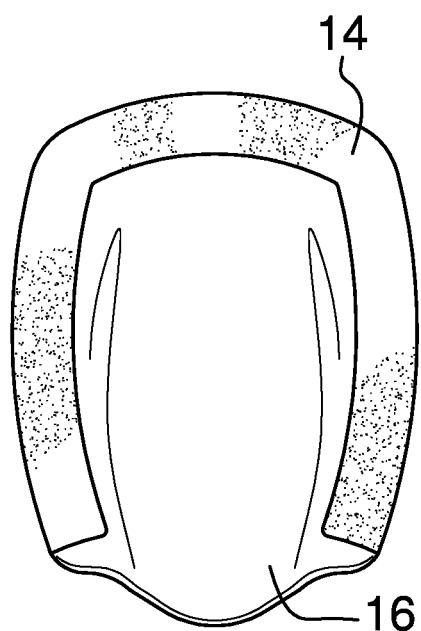
FIG. 4 is a back view of an embodiment of the disclosure.
Figure 5:
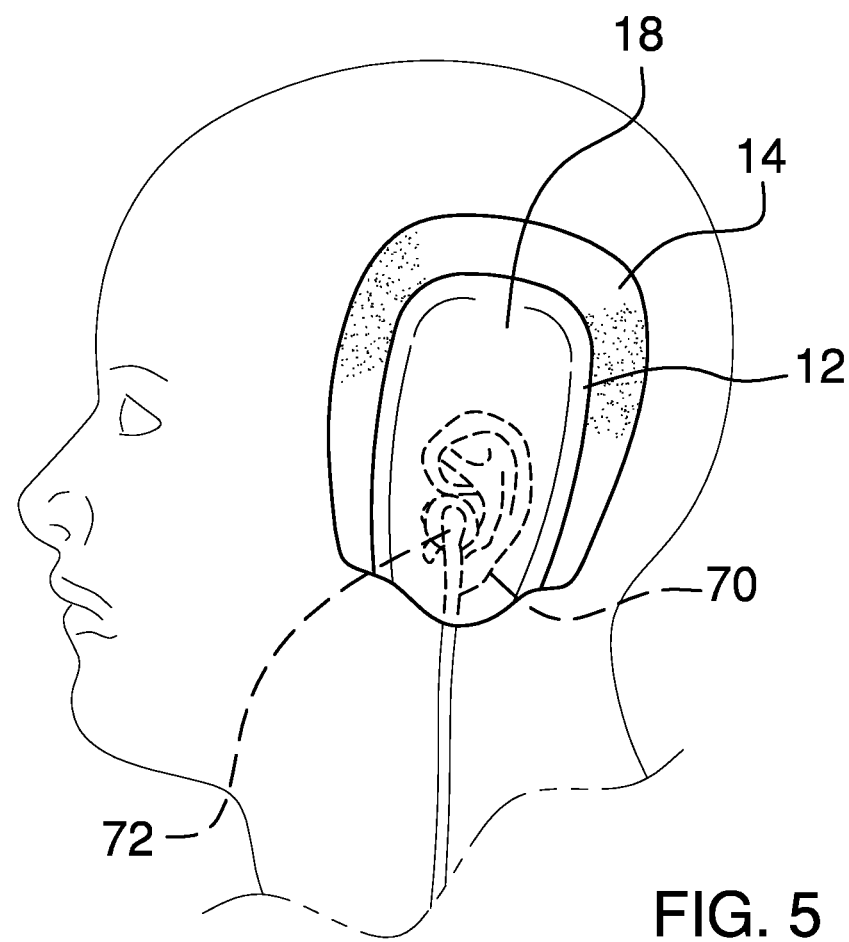
FIG. 5 is a front view of an embodiment of the disclosure.

With reference now to the drawings, and in particular to FIGS. 1 through 5 thereof, a new ear and headphone cover embodying the principles and concepts of an embodiment of the disclosure and generally designated by the reference numeral 10 will be described.

As best illustrated in FIGS. 1 through 5, the ear and ear headphone shielding assembly 10 generally comprises a panel 12 and a cushion member 14. The panel 12 has an inner surface 16 and an outer surface 18. The inner surface 16 is concavely shaped, while the outer surface 18 is convexly shaped. The panel 12 has a perimeter edge including a top edge 20, a bottom edge 22, a first side edge 24, and a second side edge 26. The inner surface 16 is configured to receive an ear 70 such that the ear 70 is adjacent to the inner surface 16. The panel 12 may be formed from a unitary structure extending from the inner surface 16 to the outer surface 18. The panel 12 comprises a rigid material such as a plastic material, but should be understood to include other rigid materials.

The inner surface 16 has a depth of less than 2.0 inches and typically greater than 0.5 inches. The depth is measured from the lowest point of the concave surface to a plane extending between and including the first side edge 24 and second side edge 26. As can be seen in the Figures, while the panel is curved from its central area to the top 20, bottom 22 and first side edges 24, the bottom edge 16 may extend generally straight down from the central area.

The cushion member 14 may be attached to the perimeter edge and is coextensive with the top edge 20, the first side edge 24 and the second side edge 26, but leaving the bottom edge 22 free of the cushion member 14. The cushion member 14 may comprise of a resiliently compressible material such as a foamed elastomer, but should not exclude other compressible materials. The cushion member 14 may extend inwardly from the perimeter edge and over the inner surface to form a lip 28.

In use, the assembly 10 is worn over a person's ear 70 when the ear has an internal headphone 72 positioned therein. Such headphones are colloquially known as "buds" or "ear buds." The assembly provides a shield between the ear and a surface, which may include a pillow, upon which a person lays their head such that the headphone 72 is not biased inward and against the ear 70. The assembly 10, in this fashion, forms a shield or barrier between the ear 70 and the surface against which the head lies to improve comfort for the user of the headphones.

With respect to the above description then, it is to be realized that the optimum dimensional relationships for the parts of an embodiment enabled by the disclosure, to include variations in size, materials, shape, form, function and manner of operation, assembly and use, are deemed readily apparent and obvious to one skilled in the art, and all equivalent relationships to those illustrated in the drawings and described in the specification are intended to be encompassed by an embodiment of the disclosure.

Therefore, the foregoing is considered as illustrative only of the principles of the disclosure. Further, since numerous modifications and changes will readily occur to those skilled in the art, it is not desired to limit the disclosure to the exact construction and operation shown and described, and accordingly, all suitable modifications and equivalents may be resorted to, falling within the scope of the disclosure. In this patent document, the word "comprising" is used in its non-limiting sense to mean that items following the word are included, but items not specifically mentioned are not excluded. A reference to an element by the indefinite article "a" does not exclude the possibility that more than one of the element is present, unless the context clearly requires that there be only one of the elements.

I claim:

1. An ear and ear headphone shielding assembly configured to receive an ear having a headphone positioned therein, said assembly comprising:

a panel having an inner surface and an outer surface, said inner surface being concavely shaped, said outer surface being convexly shaped, said panel having a perimeter edge including a top edge, a bottom edge, a first side edge, and a second side edge, said inner surface being configured to receive an ear such that the ear is adjacent to said inner surface, said bottom edge having a parabolic medial section, opposite ends of said parabolic medial section being spaced such that said parabolic medial section is configured for positioning under the ear having said opposite ends outwardly laterally spaced from front and back edges of the ear;

a cushion member being attached to said perimeter edge, said cushion member being coextensive with said top edge, said first side edge and said second side edge, said bottom edge being free of said cushion member between said opposite ends of said parabolic medial section of said bottom edge.

2. The assembly as in claim 1, said panel being formed from a unitary structure extending from said inner surface to said outer surface.

3. The assembly as in claim 2, said panel comprising a rigid material.

4. The assembly as in claim 1, said panel comprising a rigid material.

5. The assembly as in claim 3, said inner surface having a depth of less than 1.5 inches.

6. The assembly as in claim 1, said inner surface having a depth of less than 1.5 inches.

7. The assembly as in claim 1, said cushion member comprising a resiliently compressible material.

8. The assembly as in claim 3, said cushion member extending inwardly from said perimeter edge and over said inner surface to form a lip.

9. The assembly as in claim 1, said cushion member extending inwardly from said perimeter edge and over said inner surface to form a lip.

10. An ear and ear headphone shielding assembly configured to receive an ear having a headphone positioned therein, said assembly comprising:

a panel having an inner surface and an outer surface, said inner surface being concavely shaped, said outer surface being convexly shaped, said panel having a perimeter edge including a top edge, a bottom edge, a first side edge, and a second side edge, said bottom edge having a parabolic medial section, opposite ends of said parabolic medial section being spaced such that said parabolic medial section is configured for positioning under the ear having said opposite ends outwardly laterally spaced from front and back edges of the ear, said inner surface being configured to receive an ear such that the ear is adjacent to said inner surface, said panel being formed from a unitary structure extending from said inner surface to said outer surface, said panel comprising a rigid material, said inner surface having a depth of less than 1.5 inches;

a cushion member being attached to said perimeter edge, said cushion member comprising a resiliently compressible material, said cushion member being coextensive with said top edge, said first side edge and said second side edge, said bottom edge being free of said cushion member between said opposite ends of said parabolic medial section of said bottom edge, said cushion member extending inwardly from said perimeter edge and over said inner surface to form a lip.

* * * * *